US011083768B2

(12) United States Patent
Malasquez

(10) Patent No.: US 11,083,768 B2
(45) Date of Patent: Aug. 10, 2021

(54) METHOD OF MANUFACTURING A BOTANICAL BLEND INCLUDING CANNABINOIDS AND PRODUCT THEREOF

(71) Applicant: Spirit Songs Botanicals, Aurora, CO (US)

(72) Inventor: Manu Sai Malasquez, Aurora, CO (US)

(73) Assignee: Thirsty Holdings II, LLC, Denver, CO (US)

( * ) Notice: Subject to any disclaimer, the term of this patent is extended or adjusted under 35 U.S.C. 154(b) by 0 days.

(21) Appl. No.: 16/824,545

(22) Filed: Mar. 19, 2020

(65) Prior Publication Data

US 2020/0316154 A1    Oct. 8, 2020

Related U.S. Application Data

(60) Provisional application No. 62/820,746, filed on Mar. 19, 2019.

(51) Int. Cl.
| | |
|---|---|
| *A61K 36/00* | (2006.01) |
| *A61K 36/47* | (2006.01) |
| *A61K 47/44* | (2017.01) |
| *A61K 31/05* | (2006.01) |

(52) U.S. Cl.
CPC .............. *A61K 36/47* (2013.01); *A61K 31/05* (2013.01); *A61K 47/44* (2013.01); *A61K 2236/331* (2013.01)

(58) Field of Classification Search
CPC ...................................................... A61K 36/00
USPC ............................................................ 424/725
See application file for complete search history.

(56) References Cited

U.S. PATENT DOCUMENTS

2013/0046363 A1* 2/2013 Thomas ............... A61N 5/0613
607/89

* cited by examiner

*Primary Examiner* — Michael V Meller
(74) *Attorney, Agent, or Firm* — Kevin H. Fortin

(57) ABSTRACT

A cannabinoid composition comprising, purified water, hemp extract having a between 30-70% cannabidiol concentration. The hemp extract being a whole plant extract derived hemp. The composition includes 200-800 mg of ajo sacha paste dissolved in the water in a final concentration of 600 mg paste per 60 ml (2 oz) finished product. The composition further includes sangre de grado is added in the standardized aqueous commercial form at a concentration of 0.5 ml per 60 ml of finished product. The composition includes an excipient chosen from the group consisting of emulsifiers, preservatives, fragrance, flavorings, a carrier oil, and combinations thereof. A method of the invention includes adding these components together to form the composition. In particular, the method includes dissolving equal amounts of 30× Ajo Sacha paste in equal weight hot purified water. Providing a botanical carrier oil and mixing hep CBD oil, commercial Sangre de Grado solution, and Ajo Sacha solution to the botanical carrier oil.

1 Claim, No Drawings

METHOD OF MANUFACTURING A BOTANICAL BLEND INCLUDING CANNABINOIDS AND PRODUCT THEREOF

FIELD OF THE INVENTION

The present invention pertains to botanical blends including cannabinoids.

BACKGROUND AND SUMMARY OF THE INVENTION

The sulfur compounds (the predominate ones being alliin and various allyl sulfides) in both garlic and Ajo Sacha have been studied by many and reported over the years to be able to lower cholesterol. When laboratory rats were fed dried ajo sacha flowers (2% of their dietary intake), scientists reported that cholesterol levels were lowered, and much like garlic, the absorption of cholesterol in the intestines was inhibited. In 2001, a research group reported that the ajo sacha's organosulfur compounds lowered cholesterol in both humans and animals in their study.

In research published in 1980, a water extract of ajo sacha leaves was reported to have an antioxidant effect which was attributed to the anthocyanin compounds found in the plant. These antioxidant actions were independently reported by other researchers in studies published in 1995, 1997, 2009 and 2017. Several of these studies reported very strong antioxidant actions and attributed them to the isolated and tested organosulfur compounds and ursolic acid instead.

Researchers first confirmed ajo sacha's long standing use for arthritis and rheumatism when they reported that the plant was capable of inhibiting COX (an enzyme required in the inflammatory process) and well as reduced ear edema in a study with rats in 1997. Other studies were published in 2009 and 2018 confirming ajo sacha's anti-inflammatory actions. The newer research is reporting that ajo sacha's anti-inflammatory actions can also be explained by the plant's ability to modulate the immune system and reduce the production of immune cells that cause inflammation. The 2018 study additionally reported very strong pain-relieving effects in mice that should be studied further.

Ajo sacha has also been reported with antimicrobial actions against fungi, plant viruses, and bacteria which may help explain its long-standing use for colds, flu, pneumonia and other upper respiratory infections. Thirteen different studies from 1970 to 2012 have reported ajo sacha's beneficial effects against bacteria, viruses and fungi. One of these studies published in 2005 said the antifungal action of a crude ajo sacha leaf extract equaled that of a leading antifungal drug (clotrimazole) at very low dosages. These researchers also tested the leaf extract against head lice and lung cancer cells with very positive results for both at very low dosages. They summarized their research saying ajo sacha should continue to be studied for possible new anti-fungal, cancer and anti-lice drugs based on the results they achieved. In addition to killing lice, other research published in 2016 reported an essential oil of ajo sacha leaves was highly effective at both killing and repelling white flies that are a problem pest in commercial tomato crops in South America.

Ajo sacha's has been studied for its anti-cancer actions in three studies in addition to the one study referenced above. Researchers first reported in 1992 that ajo sacha's anti-cancer actions came from the well-known and well-studied anticancerous naphthoquinones chemicals found in the plant. But research published in 2015 indicates that the anticancer actions could also be coming from the organosulfur compounds. A third research group published a preliminary in vitro study in 2015 that just showed a crude leaf extract was active at low dosages against a mouse cancer cell line.

Sangre De Grado

The results of in vitro and in vivo studies largely support the majority of ethnomedical uses of sangre de drago including the treatment of diarrhea, wounds, tumors, stomach ulcers, herpes infection, the itching, pain and swelling of insect bites, and other conditions. Clinical studies of sangre de drago products have reported positive results in the treatment of traveler's and watery diarrhea and the symptoms of insect bites. Because the sap has shown low toxicity and preparations used in clinical studies were well tolerated, further clinical and pharmacologic studies are anticipated.

Sangre de grado's red sap or latex (and also its bark) has a long history of indigenous use in the rainforest and in South America. The earliest written reference dates its use to the 1600s, when Spanish naturalist and explorer P. Bernabé Cobo found that the curative power of the sap was widely known throughout the indigenous tribes of Mexico, Peru, and Ecuador. For centuries, the sap has been painted on wounds to staunch bleeding, to accelerate healing, and to seal and protect injuries from infection. The sap dries quickly and forms a barrier, much like a "second skin." It is used externally by indigenous tribes and local people in Peru for wounds, fractures, and hemorrhoids, internally for intestinal and stomach ulcers, and as a douche for vaginal discharge. Other indigenous uses include treating intestinal fevers and inflamed or infected gums, in vaginal baths before and after childbirth, for hemorrhaging after childbirth, and for skin disorders.

Scientists have attributed many of the biologically active properties of the sap (especially its wound-healing capacity) to two main "active" constituents: an alkaloid named taspine, and a lignan named dimethylcedrusine.

Of course, botanists, herbalists, and naturopaths would disagree with such reductionist conclusions (and often do); in this particular case, the matter is actually proven by science. Noted author and ex-USDA economic botanist Dr. James Duke summed this up eloquently, saying, "I like the comments on dragon's blood, and would add one further note: in addition to the proanthocyanadins (including Pycnogenol) and taspine, there's another active ingredient—dimethylcedrusine. While each of these alone—dimethylcedrusine, Pycnogenol and taspine—was shown to effectively heal wounded rats (with squares of skin exfoliated, i.e., peeled off) by European scientists, the whole dragon's blood was shown to speed healing four times faster. The whole was better than the sum of its parts. Synergy makes the whole herb stronger; diversity makes the rainforest stronger."

The wound-healing action of sangre de grado resin was first related to the taspine alkaloid in 1989. Several later studies also concentrated on the wound-healing and antitumorous properties of taspine. The lignan dimethylcedrusine was isolated by scientists in 1993 and was shown to play a central role in sangre de grado's effective wound-healing action. This Belgian study revealed that the crude resin stimulated contraction of wounds, helped in the formation of a crust/scab at the wound site, regenerated skin more rapidly, and assisted in the formation of new collagen. This was the study to which Dr. Duke referred in documenting that the crude resin was found to be four times more effective at wound healing and collagen formation than its isolated chemicals (and healed wounds 10-20 times faster than using nothing at all).

The Belgian scientists also determined that taspine was active against herpes virus in this study. In 1994 other phytochemicals were found, including phenolic compounds, proanthocyanadins, and diterpenes, which showed potent antibacterial activity (against *E. coli* and *Bacillus subtilis*) as well as wound-healing properties. Another study documented sangre de grado's antioxidant effects and researchers in Canada documented its antifungal properties. Another important traditional use of the sap was verified by clinical research in a 2000 study designed to evaluate its gastrointestinal effects. Researchers concluded that "Sangre de grado is a potent, cost-effective treatment for gastrointestinal ulcers and distress via antimicrobial, anti-inflammatory, and sensory afferent-dependent actions." In 2002, these same researchers reported that sangre de grado evidenced an in vitro effect against stomach cancer and colon cancer cells as well. In 2003 Italian researchers reported that the resin inhibited the growth of a human myelogenous leukemia cell line and also prevented cells from mutating in test tube studies In addition, several health practitioners in the U.S. indicate benefits in using sangre de grado resin internally for diabetic neuropathy because of its previously documented effects on nerve endings, nerve pain and nerve inflammation. Benefits have also been reported with diabetes-related skin ulcers and sores (applied topically) which have refused to heal using other methods Cannabidiol (CBD) Drops ("Amazon Blend").

CBD is a cannabinoid derived from *Cannabis Saliva* L. Hemp is *Cannabis Sativa* L. having less than 0.3% Tetrahydrocannabinol (THC) by weight, and is defined in the 2018 Farm Bill in the United States.

Although CBD is described in the present invention, CBD could be supplemented with any of the hundreds of cannabinoids found in *Cannabis Sativa* L. including hemp-derived cannabinoids. A cannabinoid is defined as any molecule that impacts either the CB1 or CB2 receptors in humans. *Cannabis Sativa* L, is rich in phytocannabinoids, but the term "cannabinoids" also includes synthetic cannabinoids and endocannabinoids.

The present invention can be formulated into a topical cream, an oral spray, oral tincture, or dissolvable drops for time release delivery via the oral mucosal membranes.

Further, the amounts of active ingredients, carriers, inactive ingredients can individually vary by up to 20% from each amount specified herein, whether expressed on a percentage basis, or by weight, or by volume.

The carrier oil can be synthetic or a combination of natural oils, having a preferred lipid profile.

CBD, Sangre de grado, Ajo Sacha oral combination drops for relief of pain and inflammation.

A new and novel combination of 3 reliable herbs used around the world by both indigenous and modern civilizations is now proposed to be formulated together from their complete plant derived extracts to make a synergistic medicinal supplement that is convenient and effective for the relief of pain, inflammation, wound healing, and other chronic disease states. The long and well documented history of each of the ingredients by themselves have demonstrated the viability of using these herbal treatments over hundreds of years of documented history, with the added benefit of updated pharmaceutical manufacturing processes that both enhance the concentration of active ingredients along with the added comfort of pleasing formulations to the taste and presentation for modern sensibilities. CBD products by themselves are now well tolerated and acceptable to patients around the world who provide ample testimony to their effectiveness and safety, but all products have room to improve. This novel mixture of CBD, Sangre de Grado (Dragons Blood) and Ajo Sacha (Garlic Tree) have independent biological properties that effectively assist the treatment of many chronic conditions more powerfully than any of the constituents alone.

EXAMPLE 1: 30 ML AJO SACHA/CBD TINCTURE

Spirit Song Proportions
40% CBD=400 mg per bottle
60% Ajo Sacha=600 mg per bottle
0.5 ml Sangre de Grado per bottle
Carrier Oil selected from the group consisting of: olive oil, avocado oil, coconut oil, and combinations thereof.

EXAMPLE 2: SPIRIT SONG CBD DROPS FOR ORAL DELIVERY

Details of the invention for each 1 ounce bottle:
Included in the invention are High quality, organic, CBD oil (full-spectrum CBD hemp oil contains CBD plus over 200 natural compounds and nutrients, including: Terpenes (limonene, myrcene, pinene, humulene, linalool, beta-caryophyllene, and others) with no THC, obtained from a reputable source tested for heavy metals and pesticides to achieve a total of 400 mg per bottle AjoSacha, *Mansoaalliacea*, or garlic vine, obtained from a thick paste of desiccated tar of the whole plant to deliver 600 mg of extract per bottle Sangre de grado, (*Croton lechleri*) obtained as a standardized aqueous solution to deliver 0.5 ml. extract per bottle tested for heavy metals.

All active extracts are mixed in an appropriate compounding laboratory with a Carrier Oil to allow maximum bioavailability using appropriate surfactant emulsifiers, preservatives and flavors to enhance palatability and patient acceptance.

BIO-EFFICACY AND HOW THE ELEMENTS CONTRIBUTE TO THE INVENTION

CBD oil is a major active ingredient with a litany of proven medical effects including Natural pain relief and anti-inflammatory properties, Quitting smoking and drug withdrawals, Epilepsy, neurological symptoms and disorders, Fightingcancer, Anxietydisorders, Acne, Alzheimer's disease, all documented by extensive scientific publishing AjoSacha, *Mansoaalliacea*, or garlic vine,—another well documented herbal treatment for a variety of conditions, including lower cholesterol, very strong antioxidant actions, arthritis and rheumatism, antimicrobial actions against fungi, plant viruses, and bacteria which may help explain its long-standing use for colds, flu, pneumonia and other upper respiratory infection, anti-cancer actions came from the well-known and well-studied anticancerous naphthoquinones Sangre de grado is botanically classified in the:
Family: Euphorbiaceae
Genus: *Croton*
Species: *lechleri*

Curative power of the sap: the sap dries quickly and forms a barrier, much like a "second skin", internally for intestinal and stomach ulcers, taspine was active against herpes virus in this study. In 1994 other phytochemicals were found, including phenolic compounds, proanthocyanadins, and diterpenes, which showed potent antibacterial activity (against *E. coli* and *Bacillus subtilis*), several health practitioners in the U.S. indicate benefits in using sangre de grado resin internally for diabetic neuropathy because of its previously documented effects on nerve endings, nerve pain and nerve inflammation.

As an alternative to utilizing raw sap from Sangre de grado, the sap constituents including stapine, phenolic compounds, diterpenes, proanthocyanadines, and other phytochemicals can be isolated and utilized in efficacious proportions in accordance with the present invention. These constituents can be combined with, or supplement, the raw sap to improve particular bioactivity of the present invention. The raw sap can by processed into a crystalline powder in an alternative embodiment, and the constituents can be utilized to engineer a particular consistent active constituent mix.

Fragrance, flavoring, carrier oils, preservatives are adjusted and mixed, or emulsified, with the product to provide improved taste, texture, transdermal bioavailability, and internal bioavailability.

Additives, including the constituents discussed above, can provide a longer shelf life without separation of oils and aqueous components.

Additional information of ingredients, active constituents, method of use

CBD Oil Oral Effects

CBD is one of many compounds, known as cannabinoids, in the *cannabis* plant. Researchers have been looking at the possible therapeutic uses of CBD.

CBD oils are oils that contain concentrations of CBD. The concentrations and the uses of these oils vary.

All cannabinoids, including CBD, produce effects in the body by attaching to certain receptors.

The human body produces certain cannabinoids on its own. It also has two receptors for cannabinoids, called the CB1 receptors and CB2 receptors.

CB1 receptors are present throughout the body, but many are in the brain.

The CB1 receptors in the brain deal with coordination and movement, pain, emotions, and mood, thinking, appetite, and memories, and other functions. THC attaches to these receptors.

CB2 receptors are more common in the immune system. They affect inflammation and pain.

Researchers once believed that CBD attached to these CB2 receptors, but it now appears that CBD does not attach directly to either receptor.

Instead, it seems to direct the body to use more of its own cannabinoids.

Benefits—CBD may benefit a person's health in a variety of ways.

Natural pain relief and anti-inflammatory properties

People tend to use prescription or over-the-counter drugs to relieve stiffness and pain, including chronic pain.

Some people believe that CBD offers a more natural alternative.

Authors of a study published in the Journal of Experimental Medicine found that CBD significantly reduced chronic inflammation and pain in some mice and rats.

The researchers suggested that the non-psychoactive compounds in marijuana, such as CBD, could provide a new treatment for chronic pain.

Quitting Smoking and Drug Withdrawals

Some promising evidence suggests that CBD use may help people to quit smoking.

A pilot study published in Addictive Behaviors found that smokers who used inhalers containing CBD smoked fewer cigarettes than usual and had no further cravings for nicotine.

A similar review, published in Neurotherapeutics found that CBD may be a promising treatment for people with opioid addiction disorders.

The researchers noted that CBD reduced some symptoms associated with substance use disorders. These included anxiety, mood-related symptoms, pain, and insomnia.

More research is necessary, but these findings suggest that CBD may help to prevent or reduce withdrawal symptoms.

Epilepsy

After researching the safety and effectiveness of CBD oil for treating epilepsy, the FDA approved the use of CBD (Epidiolex) as a therapy for two rare conditions characterized by epileptic seizures in 2018.

In the U.S., a doctor can prescribe Epidiolex to treat:

Lennox-Gastaut syndrome (LGS), a condition that appears between the ages of 3 and 5 years and involves different kinds of seizures Dravet syndrome (DS), a rare genetic condition that appears in the first year of life and involves frequent, fever-related seizures The types of seizures that characterize LGS or DS are difficult to control with other types of medication.

The FDA specified that doctors could not prescribe Epidiolex for children younger than 2 years. A physician or pharmacist will determine the right dosage based on body weight.

Other Neurological Symptoms and Disorders

Researchers are studying the effects of CBD on various neuropsychiatric disorders.

Authors of a 2014 review noted that CBD has anti-seizure properties and a low risk of side effects for people with epilepsy.

Findings suggested that CBD may also treat many complications linked to epilepsy, such as neurodegeneration, neuronal injury, and psychiatric diseases.

Another study, published in Current Pharmaceutical Design, found that CBD may produce effects similar to those of certain antipsychotic drugs, and that the compound may provide a safe and effective treatment for people with schizophrenia. However, further research is necessary.

Fighting Cancer

Some researchers have found that CBD may prove to combat cancer.

Authors of a review published in the British Journal of Clinical Pharmacology found evidence that CBD significantly helped to prevent the spread of cancer.

The researchers also noted that the compound tends to suppress the growth of cancer cells and promote their destruction.

They pointed out that CBD has low levels of toxicity. They called for further research into its potential as an accompaniment to standard cancer treatments.

Anxiety Disorders

Doctors often advise people with chronic anxiety to avoid *cannabis*, as THC can trigger or amplify feelings of anxiousness and paranoia.

However, authors of a review from Neurotherapeutics found that CBD may help to reduce anxiety in people with certain related disorders.

According to the review, CBD may reduce anxiety-related behaviors in people with conditions such as:

post-traumatic stress disorder general anxiety disorder panic disorder
social anxiety disorder
obsessive-compulsive disorder The authors noted that current treatments for these disorders can lead to additional symptoms and side effects, which can cause some people to stop taking them.

No further definitive evidence currently links CBD to adverse effects, and the authors called for further studies of the compound as a treatment for anxiety.

Many small-scale studies have looked into the safety of CBD in adults. They concluded that adults tend to tolerate a wide range of doses well.

Researchers have found no significant side effects on the central nervous system, the vital signs, or mood, even among people who used high dosages.

The most common side effect was tiredness. Also, some people reported diarrhea and changes in appetite or weight.

EXAMPLE 3: CBD DROPS

Each batch of Spirit Song CBD oil combination contains in a 1 ounce dropper bottle:
40% CBD=400 mg per bottle
60% Ajo Sacha=600 mg per bottle
0.5 ml Sangre de Grado per bottle
Any Carrier Oil Solution The CBD oil is obtained from a reputable dealer following all required testing, packaging, legal, and other requirements resulting in an organic highly bio available component to the final formulation.

Ajo Sacha is obtained in the form of a desiccated water soluble paste which is then dissolved in a sufficient quantity of hot water to add the aqueous solution to the carrier oil resulting in a final concentration of 600 mg paste per 60 ml (2 oz) finished product Sangre de Grado is added in the standardized aqueous commercial form at a rate of 0.5 ml per 60 ml bottle The ingredients are incorporated at the certified compounding laboratory using acceptable pharmaceutical methods with appropriate excipients such as emulsifiers, preservatives, fragrance, and flavorings, in any given carrier oil.

Standardized packaging and labeling procedures are used to create the final product.

EXAMPLE 4: CBD DROPS MANUFACTURING METHOD

Dissolve equal amounts of 30× Ajo Sacha paste in equal weight hot purified water.

Add correct amounts of CBD oil, commercial Sangre de Grado solution, and Ajo Sacha solution to the proprietary carrier oil, with necessary excipients, emulsifiers, fragrance, preservatives, and flavors, colors Blend mixture following standard pharmaceutical compounding procedures Packaging and shipping following standardized acceptable methods.

Alternative Formulation and Elements

Specific manufacturing techniques, emulsifiers, preservatives, fragrance, packaging, colors, and flavors depending on choice of third party compounding laboratory chosen may slightly change if needed. Different concentrations of active ingredients may be adjusted as experience necessitates or demand requires.

The product is administered by mouth, in the recommended dose of 2 dropperfuls, two times a day.

The active ingredients, CBD oil and Ajo Sacha have been used topically to fight infectious lesions, shrink skin growths and chronic rheumatoid arthritis, repair nerve injuries, speed healing, and stop bleeding.

Packaging would be in a variety of containers of different sizes in glass ranging from 1 oz dropper bottles up to larger sizes depending on the market.

The invention claimed is:
1. A sealed dropper bottle consisting essentially of synthetic cannabidiol, sangre de grado extract, water and ajo sacha paste.

* * * * *